United States Patent [19]

Caldarise

[11] Patent Number: 5,549,697
[45] Date of Patent: Aug. 27, 1996

[54] HIP JOINT PROSTHESES AND METHODS FOR MANUFACTURING THE SAME

[75] Inventor: Salvatore Caldarise, Hanson, Mass.

[73] Assignee: Johnson & Johnson Professional, Inc., Raynham, Mass.

[21] Appl. No.: 310,727

[22] Filed: Sep. 22, 1994

[51] Int. Cl.⁶ ........................................ A61F 2/34
[52] U.S. Cl. ......................... 623/22; 623/11; 623/16; 623/18; 623/23
[58] Field of Search ................................ 623/11, 16, 18, 623/22, 23

[56] References Cited

U.S. PATENT DOCUMENTS

| | | |
|---|---|---|
| 3,528,109 | 9/1970 | Scales . |
| 3,605,123 | 4/1969 | Hahn . |
| 3,894,297 | 7/1975 | Mittelmeier et al. ...................... 623/22 |
| 3,977,026 | 8/1976 | Battault . |
| 4,159,544 | 7/1979 | Termanini ................................. 623/22 |
| 4,281,420 | 8/1981 | Raab . |
| 4,314,381 | 2/1982 | Koeneman . |
| 4,336,618 | 6/1982 | Raab . |
| 4,365,359 | 12/1982 | Raab . |
| 4,722,870 | 2/1988 | White . |
| 4,794,046 | 12/1988 | Nagai . |
| 4,892,551 | 1/1990 | Haber ........................................ 623/23 |
| 5,041,140 | 8/1991 | Teinturier ................................. 623/23 |
| 5,080,678 | 1/1992 | Spotorno et al. ......................... 623/22 |

FOREIGN PATENT DOCUMENTS 2080118  2/1982  United Kingdom .

Primary Examiner—Mary Beth Jones
Assistant Examiner—P. Zuttarelli
Attorney, Agent, or Firm—William C. Geary, III; Lahive & Cockfield

[57] ABSTRACT

An implantable bone prosthesis, such as an acetabular shell, includes a bone engaging region that is made from a cast metal or metal alloy and an articulation surface that is formed of a ceramic material or a metal that is permanently attached to the metal bone engaging region. The bone engaging region of the prosthesis preferably includes a dampening mechanism to absorb some of the loading forces communicated to the acetabular cavity. The bone prosthesis is formed by a casting process from casting molds that are prepared using a three dimensional printing technique.

13 Claims, 3 Drawing Sheets

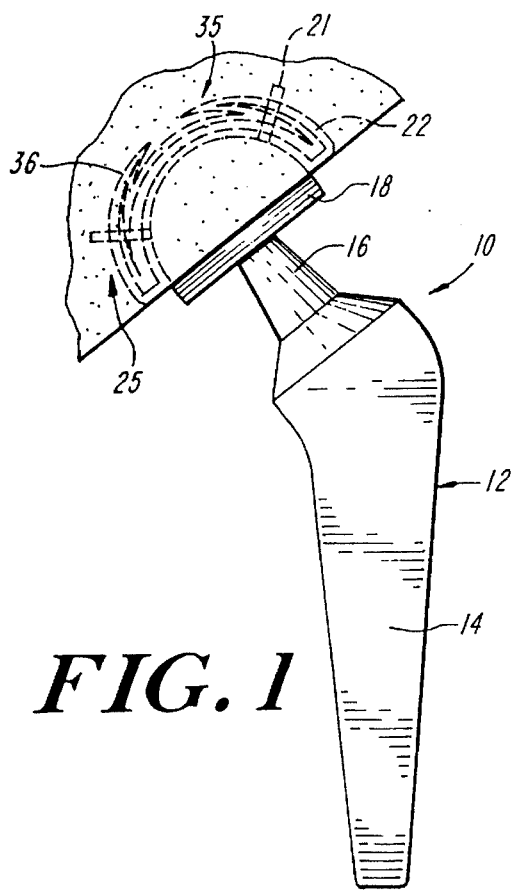
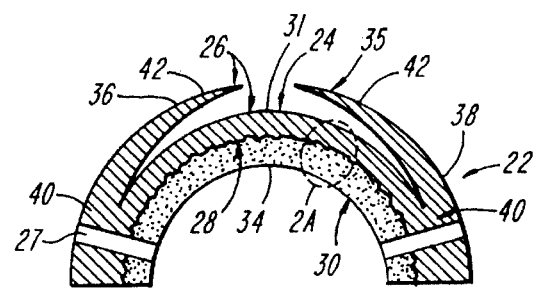
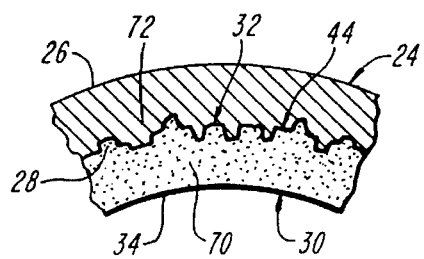
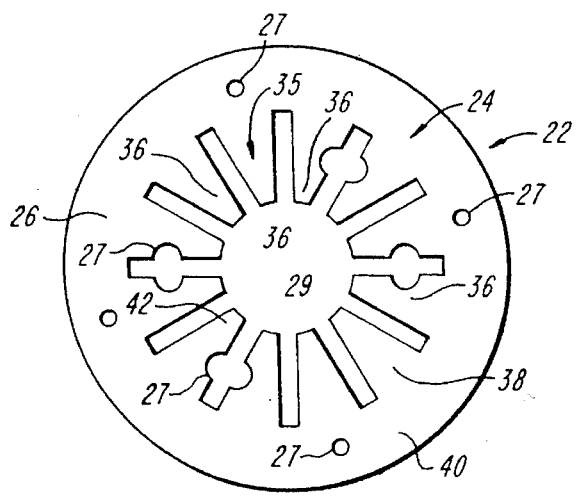
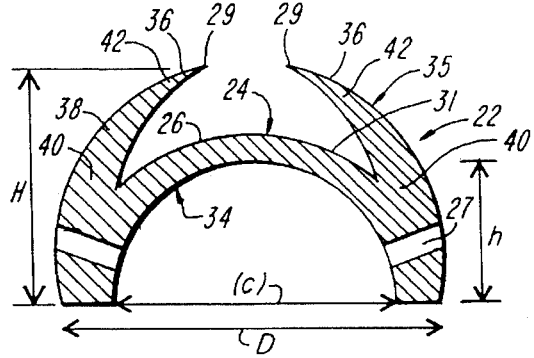
FIG. 1
FIG. 2
FIG. 2A
FIG. 3
FIG. 4

HIP JOINT PROSTHESES AND METHODS FOR MANUFACTURING THE SAME

BACKGROUND OF THE INVENTION

The present invention relates generally to the field of implantable articles. More particularly, the invention relates to bone prostheses and casting processes for manufacturing the same.

Joint replacement surgery is quite common and enables many individuals to function normally when otherwise it would not be possible to do so. Artificial joints are normally composed of metallic and/or ceramic components that are fixed to existing bone.

Artificial hip joints, for example, include several components. A femoral component of an artificial hip comprises an elongate stem or shaft at its distal end that is affixed within the medullary canal of the femur. A proximal end of the stem includes a neck region, to which is attached a femoral head. The acetabular shell is a separate component of an artificial hip joint that is affixed within existing bone such as the acetabulum. The acetabular shell includes a cup-like region that receives the femoral head. The femoral head and the acetabular shell form an articulation couple and smooth low frictional movement of the femoral head within the shell is essential to ensure proper functioning of the artificial hip joint.

Metal to metal articulation couples are often used in artificial joint construction and at least one of the articulation members is often fabricated from a low friction polymeric material. A common low friction polymeric coating material that is utilized as an articulation surface of an articulation member is ultrahigh molecular weight polyethylene (UHMWPE). UHMWPE is a durable polymer that has a very low coefficient of friction and enables smooth movement of the two components over each other.

Natural friction within a replaced, artificial joint can cause sub-micron particles of debris (e.g., metal from the joint or polymeric liner material) to become dislodged and to migrate within the joint. The phenomenon of wear debris within artificial joints is a serious problem that can inhibit the proper mechanical functioning of the joint. Wear debris can also lead to osteolysis and bone deterioration. If wear debris develops within an artificial joint it must usually be corrected by surgical removal of the debris or by subsequent replacement of the artificial joint.

The articulation couple of artificial joints is believed to be the principal source of wear debris. Currently, the state-of-the-art articulation couple in an artificial hip joint, for example, is a cobalt-chromium femoral head seated within a cobalt-chromium acetabular shell that is lined with UHMWPE. Despite this being one of the more advanced articulation couples, significant wear debris is believed to result from erosion of the polyethylene liner material.

A polymeric liner material is generally necessary to reduce friction in the joint, and these liner materials often contribute to wear debris. Although much research is focused on metal/metal articulations, current technology has not permitted the widespread use of metal/metal articulations.

Ceramic/ceramic articulation couples are believed to be potentially useful in artificial joints. Their actual use in artificial joint is, however, very limited because of the inherently low tensile strength of these materials. Ceramic materials are also quite brittle and their use as orthopedic implants, in load bearing applications, is further limited due to the risk of unpredictable catastrophic failure. See, Cooke, *Clinical Orthopaedics and Related Research*, 276:135–146 (1992). The practical use of ceramic/ceramic articulation couples also poses additional challenges with respect to fixation within bone and the manufacture of joint components having complex shapes.

Another limitation of previously known metal/metal articulations, ceramic/ceramic articulations, and metal/ceramic articulations is that there is little dampening of forces conveyed to the joint. This can place excessive loads on the joint prostheses, eventually leading to weakening or failure of the prostheses. Polymeric liners, used on the wear surface of the acetabular shell, function to some extent as a dampening mechanism by absorbing a portion of the load forces communicated to the hip joint. However, high loads and normal wear in the joint can, over time, contribute to the formation of wear debris in the joint.

Accordingly, there is a need to develop artificial joint constructions that utilize articulation couples that are improved so as to combine excellent frictional and load absorbing properties with less susceptibility to developing wear debris.

It is thus an object of the invention to provide a hip joint prosthesis that has a strong and effective low friction articulation couple. Another object is to provide an artificial joint articulation couple that greatly reduces or eliminates the tendency for wear debris to develop within the joint. It is also an object to provide a hip joint prosthesis that exhibits relatively high strength and which is effective to reduce loading forces applied to the prosthesis. A further object is to provide effective manufacturing techniques for such a hip joint prosthesis. These and other objects will be evident from the drawings and description that follow.

SUMMARY OF THE INVENTION

These and other objects are achieved by the invention which provides, in one aspect, an implantable bone prosthesis in the form of a hemispherical cup for attachment within the acetabulum cavity of the pelvis, and a method of manufacturing the same. The hemispherical cup prosthesis includes an external (with respect to the prosthesis) mounting portion that is affixed within the acetabulum cavity. The external portion preferably has a metallic dome-like structure with a textured, irregular bone-contacting surface, and an opposed mounting surface that has a concave, substantially cup-like shape. The prosthesis further includes an internal (with respect to the prosthesis) portion, that is preferably ceramic, and which receives a femoral head component of a hip joint. The internal portion includes a first surface that is permanently affixed to the mounting surface of the external portion and a second, substantially smooth articulation surface for seating the femoral head of a femur.

In another embodiment a smooth articulation surface may be formed opposite the internal dome-like structure in place of the mounting surface. Such an embodiment does not utilize a ceramic internal portion that forms the articulation surface of the acetabular shell. Instead, the acetabular shell is made entirely of metal. The articulation surface may, however, be lined with a low friction polymer such as UHMWPE.

The dome-like structure preferably includes a dampening mechanism for absorbing loading forces communicated to the hip joint. In a preferred embodiment, the dampening mechanism is in the form of a discontinuous bone-contacting surface formed of one or more leaf spring members.

The implantable prostheses of the present invention can be formed from a casting process that incorporates three-dimensional (3-D) printing techniques. 3-D printing is used to manufacture a casting mold or mold surface by building the surface of the mold up in layers. According to the 3-D printing process used in the invention, a powder material of suitable composition is laid down layer by layer, and a portion of each layer is solidified by applying a binder material in selected regions thereof. In this manner a green mold is obtained that can subsequently be dried and fired. A portion of the mold can be the internal ceramic portion of the bone prosthesis which can remain secured to the metallic dome-like structure following casting. Alternatively, the internal ceramic portion can be a separate ceramic insert that is incorporated into the mold during or prior to the 3-D printing process.

Following formation of the mold, conventional casting procedures can be implemented to form the metallic portion of the prosthesis, such as by filling the mold with a molten or powdered casting material such as a metal. Once the cast prosthesis solidifies, the expendable mold component is separated from the prosthesis by mechanical and/or chemical means. This results in a prosthesis that includes a metallic dome-like component permanently affixed to the internal ceramic component of the prosthesis. Complex structures can be incorporated into the design of the mold to achieve a cast dampening mechanism in the finished article without the need for post-processing machining. In addition, post-cast thermal treatments may be utilized to improve ductility, and thus minimize brittleness of the material.

BRIEF DESCRIPTION OF THE DRAWINGS

The foregoing and other objects, features and advantages of the invention will be apparent from the following description of a preferred embodiment of the invention illustrated in the accompanying drawings, in which like characters refer to the same parts throughout the different views.

FIG. 1 is a cross-sectional view of a femoral stem mounted within an acetabular shell of a hip joint prosthesis.

FIG. 2 is a side, sectional view of an acetabular shell constructed according to the present invention.

FIG. 2A is a detail view of a portion of the acetabular shell shown in FIG. 2.

FIG. 3 is a top perspective view of the acetabular shell of FIG. 2.

FIG. 4 is a side, sectional view of another embodiment of an acetabular shell constructed according to the present invention.

DETAILED DESCRIPTION OF THE INVENTION

Figure 5A:
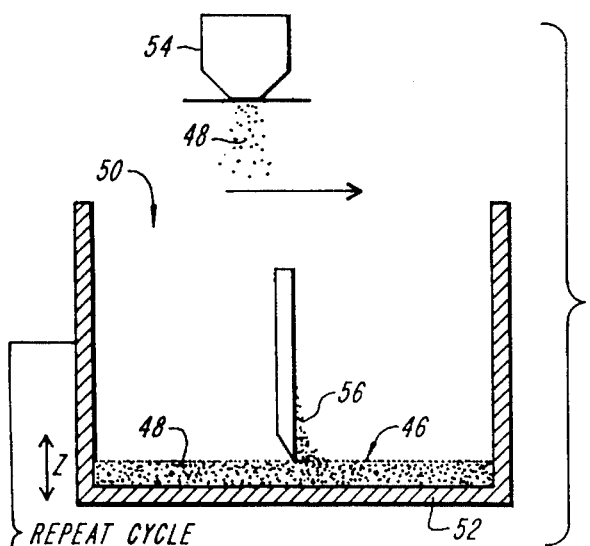
FIGS. 5A–5D illustrate the sequence of steps for making a casting mold for an implantable article according to the invention.

The invention relates to novel implantable articles and methods of making the same. The implantable articles are bone prostheses, such as articulation components of artificial joints, with improved structural and frictional properties. The bone prostheses of the invention preferably are in the form of an acetabular shell that can be used to form a hip joint having a metal/metal, a ceramic/metal or a ceramic/ceramic articulation couple.

FIG. 1 illustrates an artificial hip joint 10 that is constructed in accordance with the present invention. The artificial hip joint 10 includes a femoral component 12 mounted within an acetabular shell 22 that is affixed within the acetabulum cavity 25 of the pelvis.

The femoral component 12 is an elongate member having a stem portion 14 at a distal end and a tapered neck region 16 formed at a proximal end. As illustrated, femoral head 18 is affixed to the neck region 16 of the femoral component 12.

In one embodiment, illustrated in FIGS. 1–3, the acetabular shell 22 is constructed of separate, but permanently attached metallic and ceramic components. An external, bone-engaging portion 24 of acetabular shell 22 preferably is made of a metallic material and is affixed within the acetabular cavity 25 of the pelvis. External, bone engaging portion 24 is a substantially dome-like structure that includes an irregular bone-engaging surface 26 and a concave mounting surface 28. An internal portion 30 of acetabular shell 22 is preferably formed of a ceramic material that is generally concave and substantially cup-like in shape. A first surface 32 of the internal portion 30 of acetabular shell 22 is permanently affixed to the mounting surface 28 of acetabular shell 22. Opposite the first surface 32 of internal portion 30 is a second, substantially smooth and concave articulation surface 34 that seats and articulates with the femoral head component 18 of a hip joint.

FIGS. 2–4 further illustrate that the external, bone-engaging portion 24 of acetabular shell 22 may include a dampening mechanism 35 to absorb some of the load communicated to the hip joint. In one embodiment, the dampening mechanism can be in the form of one or more leaf spring structures 36.

As noted above, bone-engaging surface 26 of the external portion 24 of acetabular shell 22 has an irregular surface that encourages bone ingrowth and enhances fixation within the acetabulum cavity 25. Surface 26 can further include one or more screw holes 27 for seating bone screws 21.

In another embodiment, illustrated in FIG. 4, acetabular shell 22 can be made entirely of metal and includes a dampening mechanism 35 that can be in the form of leaf springs 36. The acetabular shell 22 shown in FIG. 4 may include a metallic articulation surface 34. However, such an all-metal acetabular shell may optionally include a polymeric liner material (not shown), such as ultrahigh molecular weight polyethylene, disposed upon articulation surface 34.

The term "leaf spring", as used herein, refers to each of a plurality of resilient support structures that function as a dampening mechanism. As illustrated in FIGS. 1 through 4, the leaf springs 36 are arch-like, cantilevered structures having a substantially rigid end 38 that is integral with a peripheral or equator region 40 of the acetabular shell 22. An opposite end 42 of each leaf spring 36 extends upwardly and inwardly of peripheral region 40 of acetabular shell 22. Each leaf spring preferably is spaced apart from adjacent leaf springs by a suitable distance ranging from 1 to 10 mm. Further, the leaf springs 36 form a discontinuous external surface of acetabular shell 22 such that a terminal portion 29 of each leaf spring 36 is spaced apart from the terminal portion of adjacent leaf springs 36 and apart from nominal external surface 31. Thus the leaf springs 36 form, in combination with each other and in relation to the acetabular shell, a discontinuous, hemi-spherical bone-engaging surface.

Certain features and properties of the leaf spring component of the present acetabular shell will vary depending upon the performance characteristics required of the prosthesis. One of ordinary skill in the art will be able to determine the optimal number of leafs to include in an acetabular shell made according to the invention, as well as the desired spacing between the leaf springs. The leaf deflection under varying loads and the displacement of the inner geometry of the leaf spring members are also factors that will be determined by one of ordinary skill in the art in developing a suitable prosthesis according to the invention.

As noted, the resilient, free end 42 of each leaf spring 36 extends outwardly from the equator or peripheral region 40 and arches over the acetabular shell 22 towards its apex, as shown in FIGS. 2–4. The leaf springs 36 are spaced from the nominal internal surface 31 by a distance that determines the amount of dampening that will occur. One of ordinary skill in the art will appreciate that the optimal degree of dampening will depend on the size of the acetabular shell, as well patient loading and demand. At the same time, one must consider that slip at the component/bone interface should be minimized while still providing sufficient dampening.

In a preferred embodiment, the terminal portion 29 of leaf springs 36 are separated from the nominal internal surface 31 at the terminal portion 29 by a selected distance between 0.5 mm and 5 mm, and most preferably about 2 mm. The distance between the leaf spring 36 and the nominal internal surface 31 gradually decreases in the direction approaching peripheral region 40. Further, those of ordinary skill will recognize that the orientation of the leaf spring members can be reversed. That is, the rigid end of the leaf springs can be attached to the acetabular shell terminal portion, and the leaf spring free end can extend outwardly therefrom and arches over the shell towards the peripheral portions of the shell. The leaf springs can also be configured in such a manner that they extend outward from the apex and inward from the equator in an alternating fashion.

It is understood that leaf springs 36 serve only as one example of a suitable dampening mechanism 35. One of ordinary skill in the art may substitute for leaf springs 36 other resilient mechanical dampening mechanisms that form part of the bone engaging surface 26 of the acetabular shell to reduce the level of load communicated to the hip joint.

As illustrated in FIG. 1, the femoral head 18 fits within the acetabular shell 22. The femoral head 18 and the concave articulation surface 34 of the acetabular shell 22 form the articulation couple of the artificial hip joint 10. Generally, the femoral head 18 can be manufactured from a ceramic or a metallic material. The concave articulation surface 34, as noted above, preferably is ceramic, but can also be metal or a UHMWPE-lined metal. The inherent resilience of leaf springs 36 helps to dampen the load communicated to the hip joint 10 along the axis of the femur, thus making it more feasible to use a ceramic/ceramic, metal/metal, or a ceramic/metal articulation couple. Dampening the load in the joint should make the use of these materials more attractive.

In a preferred embodiment, illustrated in FIGS. 1, 2 and 2A, the internal portion 30 of acetabular shell 22 is made of a ceramic material and the external portion 24 of acetabular shell 22 is made of a metal or metal alloy. It is also preferred that the mounting surface 28 of external portion 24 and the first surface 32 of internal portion 30 have interlocking regions 44 that enhance the permanent fixation of the two surfaces to each other.

One of ordinary skill in the art will appreciate that the dimensions of the acetabular shell of the present invention will vary. Generally, the range of dimensions is as follows:

| Outside Diameter (D) | 38 mm to 72 mm |
| Internal Cup Diameter (d) | 22 mm to 32 mm |
| Overall Height (H) | 15 mm to 45 mm |
| Nominal Height (h) | 15 mm to 40 mm |

Given the dimensions of the acetabular shell, particularly the cup diameter (d), one of ordinary skill in the art can readily determine the corresponding dimensions required of the hip head of the femoral component.

An acetabular shell of the type described above is preferably manufactured through a casting technique that relies upon specialized processes to produce a suitable casting mold. A preferred method of manufacturing such an acetabular shell is to utilize a computer controlled three dimensional ("3-D") printing technology to manufacture casting molds for directly casting the acetabular shell. The casting molds can then be used to cast the external, metallic dome-like structure and dampening mechanism of the acetabular shell. In a preferred embodiment, the ceramic internal portion 30 of the acetabular shell 22 is made directly through 3-D printing and forms a non-disposable component of the mold. Following casting, the ceramic internal portion 30 of the shell is permanently attached to the mounting surface 28 of the external metallic dome-like structure of the shell. The ceramic internal portion 30 of the shell remains secured to the metal portions of the acetabular shell 22 after disposable mold components are fractured and removed.

During the 3-D printing process, the casting mold is formed of loose powder that is applied in successive layers, with binder selectively applied to each layer by a computer-controlled scanning nozzle similar to an ink jet. The application of binder to the powder layers selectively solidifies the powder in each layer in a region or profile corresponding to a section of the desired three-dimensional solid.

Suitable three-dimensional printing techniques for the practice of the invention are disclosed in U.S. Pat. No. 5,204,055 to Sachs et al., which patent is expressly incorporated herein by reference.

The 3-D mold printing process involves the deposition of a layer of a powder material in a confined area and the application of a binding material to selected regions of the powder layer to solidify the powder in desired regions. A next layer of powder is then deposited over the first layer, and binder material is again applied to selected, generally partially overlapping regions of the second layer of powder to solidify the second layer in those new regions and to bind the solidified sections to the previously solidified sections of the first layer. These steps are repeated according to a predetermined pattern to obtain an object formed of many successive laminations of powder and binder material. The regions in which binder material is deposited in each scan layer correspond to the sections, at the current scan height, of the three-dimensional object being formed. As described further below, the object to be formed is a casting mold that represents a negative image of an implantable article to be cast.

In one embodiment, as noted above, the casting mold includes disposable and non-disposable portions. The non-disposable portion of the casting mold represents ceramic internal portion 30 of the acetabular shell 22. Ceramic internal portion 30 preferably is directly formed by the same 3-D printing process. However, a more densely packed powder material generally is used to obtain a suitably strong ceramic component that is to be joined to the implantable article to be cast.

In another embodiment, where the ceramic internal portion 30 is a separate insert, it is inserted in a split mold before the formation of the metallic components. One of ordinary skill in the art will readily appreciate that the preferred ceramic component be almost fully dense and be formed of fine grain size ceramic forming powders. The ceramic should also possess superior bust strength, suitable hardness for orthopedic applications, high surface finish and sphericity, and good fatigue strength.

Three dimensional printing processes are generally computer controlled. Virtually any design that can be scanned or interpreted by a computer may be reproduced, regardless of its complexity, subject to the resolution limit of a 3-D printing apparatus. Resolution for a powder consolidated 3-D printer discussed below currently can prepare structures with surface details as small as about 0.007 inch. However, further process improvement may reduce this value.

A preferred 3-D printing apparatus useful in practicing the present invention is available from Soligen, Inc. of Northridge, Calif. as model DSPC-alpha version.

A method of making a bone prosthesis, such as acetabular shell 22, according to the invention is illustrated in FIGS. 5A–5D. The process begins with the deposition of a layer 46 of powder material 48 in a confined region 50, as shown in FIG. 5A. The confined region 50 is defined on the surface of a stage or platen 52 which is movable in a feed direction, indicated by axis Z, perpendicular to the plane of the platen. Motion along the feed direction allows the platen 52 either to receive additional layers of powder material 48 or to permit removal of the finished part. The powder material 48 is deposited in a very thin layer within a contour in the confined region which is preferably selected to encompass either a longitudinal or transverse cross-sectional profile of a mold for forming the desired bone prosthesis. Each layer of powder 46 is preferably not more than approximately 0.007 inch thick and the powder generally is deposited so it is relatively loosely spread from a powder dispensing mechanism 54 located over the confined region. A leveling device (not shown), such as vibrating rollers, is activated to smooth out the layer and assure that the layer has a uniform thickness in the range of about 0.007 inch.

The powder material 48 can be any material which is capable of being solidified upon the application of a binder in forming a casting mold. Typical powder materials used in the method of the invention are ceramic-forming materials, such as alumina, silica, silicon carbide, silicon nitride, zirconia powders, and other materials and mixtures thereof. The powder material can also be mixed with materials that may act as fluxes or mold conditioners, such as are generally employed in making ceramic molds or in investment casting. Suitable materials are described in U.S. Pat. No. 5,204,055 (Sachs, et al.).

Figure 5B:
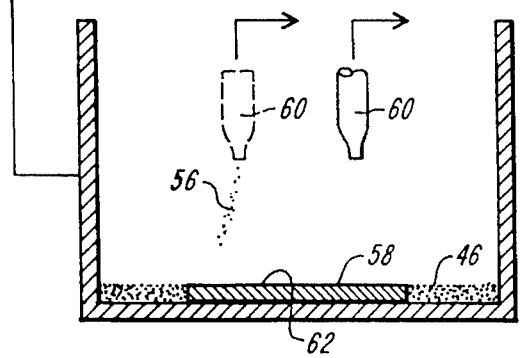
Figure 5C:
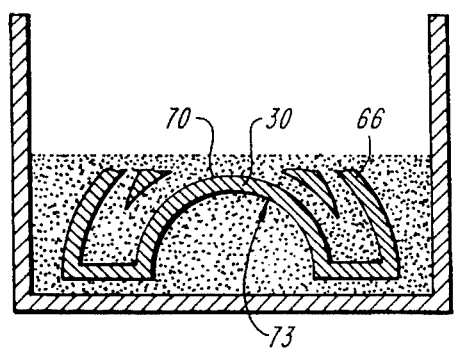

As shown in FIG. 5B, after deposition of a uniform unconsolidated powder layer 46, a binder material 56 is deposited onto selected regions 58 of the powder layer 46 according to a pattern which is defined by the desired cross section of the dimensions of the implantable article to be formed at a given location and the surface features to be imparted to the article. Preferably the binder material 56 is dispensed from a deposition mechanism 60, that operates in a manner similar to an ink-jet print head. The deposition mechanism 60 preferably has relatively fine resolution that is appropriate to the level of complexity and detail to be attained in the article to be cast from the mold.

The deposition mechanism 60 is controllably scanned, e.g., by an appropriate carriage and stepper drive, over the powder area to define an image-wise pattern 62 of binder material 56. As with conventional image-printing techniques, the deposition mechanism 60 may include means for adding a microdeflection or offset to the liquid nozzle so as to effectively print with half-dot resolution.

The binder material 56 may be any organic or inorganic binder material which will wet or react with and solidify the powder material to which it is applied. Typical binder materials may include cellulosic and butyral resins, polycarbosilazane and silicate-based materials, and other liquids normally used as binders for forming ceramic molds. Aqueous colloidal silica is the presently preferred binder material for applications that require the powder to be solidified and fired into a solid ceramic.

The powder deposition and binder material application steps of FIGS. 5A and 5B are repeated as each powder layer is solidified in the selected regions according to the predetermined scan actuation pattern. The platen 52 is moved along the Z axis perpendicular to the plane of the platen a distance equal to the thickness of the powder layer 46 with each scan to permit the deposition of a new powder layer and application of binder material to the new layer. The solidified sections of each successive powder layer are bonded to at least a portion of the solidified regions in the powder layer immediately below so that the entire multi-layer deposition and scan process defines a single, continuous three-dimensional object composed of numerous thin ring-laminations of powder material to form a solid shell. Computer control of the 3-D printing process can regulate the printing of disposable mold components or the non-disposable ceramic insert. For example, a programmable controller (not shown) can regulate the types of powder dispersed (densely packed or loose) and can regulate the binder deposition necessary to print disposable or non-disposable mold components. The process yields a complete mold 64 (shown in FIG. 5D) having disposable regions 87 and non-disposable, densely packed ceramic region 70.

In the exemplary process illustrated in FIGS. 5A–5D, alumina powder is used to form layers 46 and silica is used as the pattern solidifying binder material 56. A green (i.e., unfixed) casting mold 64 is prepared in the form of the negative image of the acetabular shell of the invention, in which an implantable acetabular shell may be formed.

Figure 5D:
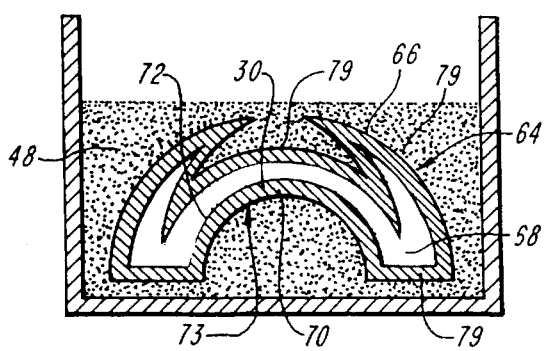

Casting mold 64, illustrated in FIG. 5D, includes a ceramic shell 66 that defines a mold cavity 68. A lower portion of the mold 64 includes a densely packed ceramic region 70 that forms articulation surface 34 of acetabular shell 22. Preferably, ceramic region 70 includes an irregular surface 72 that is adjacent to the interior of the mold. During a casting process, a casting material, such as molten metal, fills cavity 68. Upon cooling, the casting material becomes permanently affixed to irregular surface 72 of densely packed ceramic region 70. Following cooling of the cast metal, the disposable portions 79 of ceramic shell 66 are removed from around the cast article. The cast article that remains is of the type shown in FIGS. 2 and 2A in which the densely packed ceramic region 70 remains permanently attached to the metallic internal portion 30 of the acetabular shell. The densely packed ceramic portion 70 preferably forms the articulation surface 34 of the acetabular shell.

One of ordinary skill in the art will appreciate that irregular surface 72 can take a variety of forms as necessary to ensure that ceramic region 70 is permanently affixed to a cast metal component of the acetabular shell. Irregular surface 72 may be in the form of a roughened surface, or it may be in the form of protruding regions that are intended to positively interlock with the cast metal component.

Once the mold 64 is printed, loose powder material 48 which is not solidified or bonded within the casting mold is removed from the casting mold. The mold may be shaken to dislodge and remove the loose powder, or it may be immersed in a bath or solvent in which the loose powder material is washed away or dissolved while the solidified portions of the mold remain. Loose powder material which is difficult to remove completely because of its location within the casting mold may be more readily removed by subjecting the casting mold to ultrasonic or other high-frequency vibration, followed by or concurrently with immersion in a bath or solvent. Ultrasonic vibration, microwave boiling, and/or immersion in a bath or solvent are techniques that are particularly useful to remove the confined loose particles by dislodging and floating away the particles. Leaching agents such as sodium hydroxide can also be used to attack and remove ceramic materials without affecting the metal material.

After the loose powder material is removed from the casting mold, the hollow casting mold 64 is preferably baked to drive off volatile material, and fired in a furnace at a suitable temperature for a suitable time to yield a strong ceramic mold. A preferred powder material for forming the mold is alumina which, when solidified with an application of aqueous colloidal silica as a binder material, may be fired at about 1925° F. for approximately two hours to form a fired alumina casting mold. The fired casting mold is extremely strong and thermally stable so that it defines a precise mold cavity.

Depending on the degree of ceramic consolidation that is desired for proper mold strength, a certain amount of shrinkage may be expected on firing the green ceramic. Accordingly, those having ordinary skill in the art will readily appreciate that mold shrinkage can be compensated for by forming molds enlarged by a scale factor over the size of the article which is ultimately to be cast therein. Preferably, the molds have dimensions that are equivalent to approximately 2 percent larger than the dimensions of the article to be cast.

After firing, the hollow mold 64, receives a molten metal or metal alloy which is allowed to solidify to form the prosthesis. Suitable metal alloys include, but are not limited to, cobalt-chromium alloys, titanium-vanadium alloys, stainless steel and other materials that are well known for use in the manufacture of implantable prostheses.

It is understood that for some casting shapes the mold may be filled with a metal or metal alloy powder rather than a molten metal or metal alloy. In such an application heat is subsequently applied to solidify the casting according to well known techniques.

After a casting, the implantable bone prostheses are removed from the casting mold(s) as finished product. Where the casting mold is green, i.e., unfired, it is readily crumbled and destroyed and separated from the prostheses. A fired ceramic casting mold may be provided with one or more sections which are joined to form the prostheses and that can be separated as needed to remove the finished product. As noted above, ultrasonic cleaning and selective etching may used to remove all residues of the mold from the cast metal article. The mold ceramic is more permeable and less dense than the ceramic insert and thus the two can be cleanly separated from each other.

Although not specifically described herein it is understood that the cast articles may be manufactured according to the process of this invention with desired surface textures that can also be prepared by 3-D printing techniques.

The implantable article of the invention can also be manufactured by direct 3-D printing of the metal component.

Figure 6A:
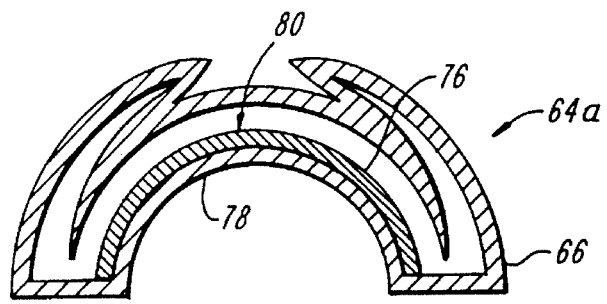
FIGS. 6A–6C illustrate casting molds for an acetabular shell prepared according to the invention.
Figure 6B:
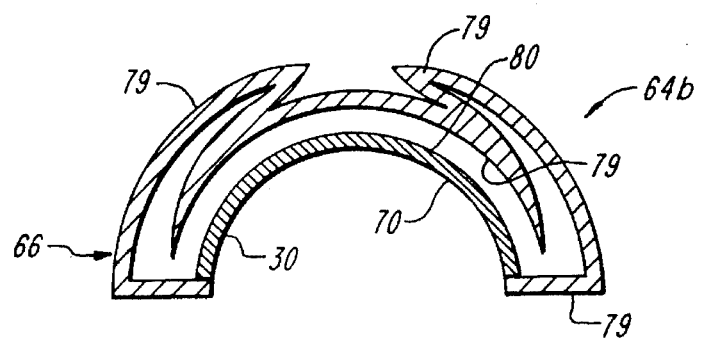
Figure 6C:
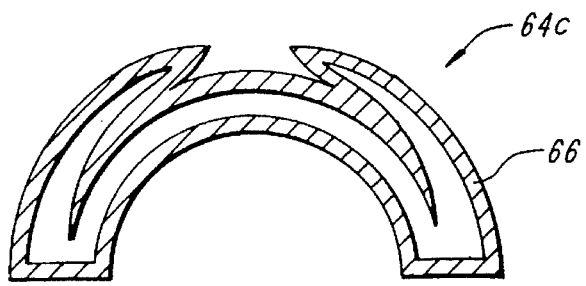

FIGS. 6A–6C show three different completed casting molds 64a, 64b, 64c for an acetabular shell that can be manufactured according to the present invention. FIG. 6A shows a complete mold 64a that has mounted therein a ceramic insert 76. Ceramic insert plate 76 may be deposited on a lower portion 78 of ceramic shell 66 as the mold is being formed by a 3-D printing process. Thereafter, the remaining portion of the shell 66 may be built up to form completed mold 64a. Preferably, surface 80 of ceramic insert plate 76 includes a textured surface to ensure permanent attachment to an article formed within the mold. In one embodiment the textured surface may be in the form of protrusions and other shapes that positively interlock with the article upon solidification of the casting material.

Casting mold 64b, shown in FIG. 6B, includes a ceramic shell 66 that includes disposable mold components 79 and non-disposable ceramic insert 70, all of which are formed by 3-D printing. A concave dome portion 82 of the ceramic insert 70 (which is equivalent to external portion 30 shown in FIGS. 2 and 2A) is made of a densely packed ceramic or ceramic forming material such as alumina, zirconia and silicon nitride. Surface 80 of ceramic insert 70 preferably has a texture similar to that described above with respect to FIG. 6A. The disposable portions 79 of shell 66 can be made of less densely packed ceramic or ceramic forming material which may be the same as or different than the material from which insert 70 is made. Following a casting process and solidification of the casting material ceramic shell portions 84 are fractured and removed while portion 82 remains integrally secured to the cast article.

Mold 64c, illustrated in FIG. 6C, is intended to be used in manufacturing a cast article, such as an acetabular shell, that is made entirely from a casting material, such as a metal. In one example the article to be cast in mold 64c is an acetabular shell made entirely of a metal or metal alloy. Ceramic shell 66 of mold 64c preferably is made entirely of the same ceramic or ceramic forming material. Ceramic shell 66 is completely disposable and is fractured from around the cast article following solidification of the cast article.

The foregoing description of methods of manufacture illustrative embodiments is presented to indicate the range of constructions to which the invention applies. Variations in the physical architecture and mold processes of the present invention will be apparent to those skilled art based upon the disclosure herein, and such variations are considered to be within the scope of the invention in which patent rights are asserted, as set forth in the claims appended hereto.

What is claimed is:

1. An implantable bone prosthesis in the form of a substantially hemispherical cup for attachment within the acetabulum cavity of the pelvis, the prosthesis comprising:

an external portion for mounting within the acetabulum cavity including a metallic dome-like structure having a textured, irregular bone-contacting surface, the bone-contacting surface further including a discontinuous portion forming a substantially hemispherical dampening structure for absorbing loading forces communicated to the acetabular cavity and a mounting surface having a substantially cup-like shape; and an internal portion for receiving a femoral had of a femur having a substantially cup-like shape and being formed of a biologically compatible ceramic or metallic material, the internal portion having a first surface that is permanently affixed to the mounting surface of the external portion and a second, substantially smooth articulation surface for seating the femoral head.

2. The prosthesis of claim 1 wherein the discontinuous bone-contacting portion forming the dampening structure is formed of one or more leaf spring members.

3. The prosthesis of claim 1 wherein the internal portion is formed of a biologically compatible ceramic material selected from the group consisting of alumina, silica, silicon carbide, silicon nitride, zirconia, and mixtures thereof.

4. The prosthesis of claim 1 wherein the external portion is formed of a biologically compatible metallic material selected from the group consisting of cobalt-chromium alloy, titanium-vanadium alloy, and stainless steel.

5. An implantable bone prosthesis in the form of a substantially hemispherical cup for attachment to the acetabulum cavity of the pelvis, the prosthesis comprising:

a metallic dome-like structure for mounting within the acetabulum cavity including a textured, irregular bone-contacting surface and a substantially smooth articulation surface having a substantially cup-like shape for seating a femoral head of a femur; and a substantially hemispherical dampening structure for absorbing loading forces communicated to the acetabulum cavity, the dampening structure being formed by one or more discontinuities in the bone-contacting surface of the metallic dome-like structure.

6. The prosthesis of claim 5 wherein the discontinuities in the bone-contacting surface comprise one or more leaf spring structures.

7. An implantable artificial hip joint comprising:

a femoral component having an elongated shaft with a neck at a proximal end thereof;

a hemispherical femoral head having a smooth outer articulation surface adapted to seat within an acetabular shell and a second surface adapted to be secured to the neck of the femoral component; and an acetabular cup for attachment to the acetabulum cavity of the pelvis, including (i) an external portion for mounting within the acetabulum cavity, the internal portion including a metallic dome-like structure having a textured, irregular bone-contacting surface and a mounting surface having a substantially cup-like shape, the bone-contacting surface further including a discontinuous portion forming a substantially hemispherical dampening structure for absorbing loading forces communicated to the acetabulum cavity; and (ii) an internal portion for receiving a femoral head of a femur having substantially cup-like shape and being formed of a biologically compatible ceramic material, the internal portion having a first surface that is permanently affixed to the mounting surface of the external portion and a second, substantially smooth bearing surface for seating the femoral head.

8. The joint of claim 7 wherein the discontinuous portion of the bone-contacting surface forming the dampening structure is formed of one or more leaf spring structures.

9. The joint of claim 7 wherein the internal portion is composed of a ceramic material selected from the group consisting of alumina, silica, silicon dioxide, silicon nitride, zirconia, and mixtures thereof.

10. The joint of claim 7 wherein the external portion is formed of a biologically compatible metallic material selected from the group consisting of cobalt-chromium alloy, titanium-vanadium alloy, and stainless steel.

11. An implantable bone prosthesis, comprising a substantially hemispherical cup-like structure for attachment within the acetabulum cavity of the pelvis, the hemispherical cup-like structure including a dome-like external, bone engaging surface and an opposed internal concave surface;

a dampening structure formed in the dome-like external, bone engaging surface for absorbing loading forces communicated to the acetabulum cavity, the dampening structure being in the form of one or more discontinuities formed in the dome-like portion of the bone engaging surface; and a polymeric liner material joined to the internal concave surface of the hemispherical cup-like structure.

12. The prosthesis of claim 11 wherein the discontinuities formed in the bone-engaging surface forming the dampening structure comprise one or more leaf spring members.

13. The prostheses of claim 11 wherein the polymeric liner material is ultrahigh molecular weight polyethylene.

* * * * *